United States Patent
Roeper et al.

(10) Patent No.: US 8,234,767 B2
(45) Date of Patent: Aug. 7, 2012

(54) PROCESS FOR MANUFACTURING PACKAGED LANCETS AND DEVICE FOR ANALYZING BODY FLUID

(75) Inventors: Josef Roeper, Neuhofen (DE); Werner Finke, Einhausen (DE); Herbert Harttig, Neustadt (DE); Bernd Hiller, Lampertheim (DE); Hans List, Hesseneck-Kailbach (DE)

(73) Assignee: Roche Diagonostics Operations, Inc., Indianapolis, IN (US)

( * ) Notice: Subject to any disclaimer, the term of this patent is extended or adjusted under 35 U.S.C. 154(b) by 197 days.

(21) Appl. No.: 12/726,534

(22) Filed: Mar. 18, 2010

(65) Prior Publication Data
US 2010/0222799 A1    Sep. 2, 2010

Related U.S. Application Data

(63) Continuation of application No. PCT/EP2008/007875, filed on Sep. 19, 2008.

(30) Foreign Application Priority Data

Sep. 19, 2007  (EP) .................................. 07018338

(51) Int. Cl.
- *B21D 39/00* (2006.01)
- *A61B 5/00* (2006.01)
- *B65B 51/22* (2006.01)

(52) U.S. Cl. ...... 29/418; 29/458; 29/525.13; 29/525.14; 29/525.15; 436/44; 600/583; 606/181; 53/463

(58) Field of Classification Search ............... 29/413, 29/414, 415, 458, 525.13, 525.14, 525.15, 29/418; 436/44; 600/583; 606/181; 53/463
See application file for complete search history.

(56) References Cited

U.S. PATENT DOCUMENTS

| | | |
|---|---|---|
| 3,665,672 A | 5/1972 | Speelman |
| 3,685,249 A | 8/1972 | Jackson |
| 4,945,203 A | 7/1990 | Soodak et al. |
| 4,999,582 A | 3/1991 | Parks et al. |
| 5,318,584 A | 6/1994 | Lange et al. |
| 5,334,195 A | 8/1994 | Gollobin |
| 5,857,983 A | 1/1999 | Douglas et al. |
| 5,879,311 A | 3/1999 | Duchon et al. |
| 6,036,919 A | 3/2000 | Thym et al. |

(Continued)

FOREIGN PATENT DOCUMENTS

CH    327555 A    1/1958
(Continued)

OTHER PUBLICATIONS

CH 327555 A Machine Translation.
(Continued)

*Primary Examiner* — Jermie Cozart
(74) *Attorney, Agent, or Firm* — Woodard, Emhardt, Moriarty, McNett & Henry LLP (57) ABSTRACT

Disclosed is a process for manufacturing packaged lancets. The steps of the process include providing a tape comprising a plurality of lancets comprising a lancet tip and a lancet body, enveloping at least the lancet tip with at least one foil, whereby the at least one foil forms a first and a second portion that overlap at least partly, and sealing the at least one foil with a laser beam at least at the edges of the first and second portion of the overlapping foil.

15 Claims, 8 Drawing Sheets

U.S. PATENT DOCUMENTS

| | | |
|---|---|---|
| 6,506,575 B1 | 1/2003 | Knappe et al. |
| 6,866,675 B2 | 3/2005 | Perez et al. |
| 2003/0211619 A1 | 11/2003 | Olson et al. |
| 2004/0163987 A1 | 8/2004 | Allen |
| 2005/0245845 A1 | 11/2005 | Roe et al. |
| 2006/0079810 A1 | 4/2006 | Patel et al. |
| 2006/0200045 A1* | 9/2006 | Roe ............... 600/583 |
| 2007/0167869 A1 | 7/2007 | Roe |
| 2007/0278097 A1 | 12/2007 | Bhullar et al. |
| 2010/0021342 A1 | 1/2010 | Joseph et al. |

FOREIGN PATENT DOCUMENTS

| | | |
|---|---|---|
| CN | 1489542 | 4/2004 |
| DE | 28 03 345 B1 | 6/1979 |
| EP | 0 565 970 B1 | 6/1994 |
| EP | 0 230 472 B2 | 12/2000 |
| EP | 1 360 935 A1 | 11/2003 |
| EP | 1 508 304 A1 | 2/2005 |
| EP | 1 770 014 A2 | 4/2007 |
| WO | WO 92/15988 A1 | 9/1992 |
| WO | WO 98/16430 A1 | 4/1998 |
| WO | WO 02/064439 A1 | 8/2002 |
| WO | WO 03/035479 A1 | 5/2003 |
| WO | WO 2005/080207 A1 | 9/2005 |
| WO | WO 2006/082106 A1 | 8/2006 |
| WO | WO 2006/092281 A2 | 9/2006 |

OTHER PUBLICATIONS

DE 28 03 345 B1 English Language Translation.
International Patent Application PCT/EP2008/007875 International Search Report mailed Mar. 9, 2009.

* cited by examiner

PROCESS FOR MANUFACTURING PACKAGED LANCETS AND DEVICE FOR ANALYZING BODY FLUID

CROSS REFERENCE TO RELATED APPLICATION

This application is a continuation of International Application No. PCT/EP2008/007875, filed Sep. 19, 2008, which claims the benefit of European Patent Application No. EP 07 018 338.9, filed Sep. 19, 2007, the entire disclosures of which are hereby incorporated by reference.

BACKGROUND

The present invention relates generally to processes for sealing medical devices like biosensors, test elements, or pricking devices like lancets or needles.

Medical devices like test elements or biosensors for measuring the presence or concentrations of selected analytes in test samples are well known. The same applies for pricking elements like needles, lancets or blades. Typically, these medical devices are packaged and stored in a sterile surrounding. Especially the pricking elements have to be kept sterile until they are used. There are many different ways described in the prior art how to package lancets in a sterile surrounding.

In the document US 2004/0163987 a sealing process of medical devices like lancets is described. Here the sealing is reached by using a heat or pressure sensitive adhesive.

In the application EP 1508304 are also described adhesives which might be heat-activated or pressure sensitive. In general the manufacturing process for packaged lancets is conducted by lamination techniques. Procedures like screen printing, slot coating are also mentioned for packaging lancets. The adhesive materials might be laser scribed or punched before these lamination processes.

In a further patent application, US 2006092281, a sealing of lancets which might be combined to test elements is also described by adhesive or heat sealing.

All the manufacturing processes have the disadvantage that additional material like the adhesive is used to bond the packaging material surrounding the lancets. These additional materials might contaminate the lancet. An additional disadvantage of the adhesive or the heat sealing is the fact that with these processes only a laminar sealing or joining process is achieved. This laminar process needs much space surrounding the lancets which is especially disadvantageous if the lancets should be stored in a magazine. The sealing line couldn't be narrowed because otherwise the sealing process wouldn't be complete and no sterile surrounding for the lancet is reached. Moreover, an automatic removal of the sterile packaging during the use of the system can be achieved by pricking the lancet through the sterile cover. However, it has been shown that the needle tip is often damaged by pushing the needle through such a packaging as described above. In particular if small and thin lancets are used for a painless pricking step a damaging of the needle tip is likely.

So there is a need for a reproducible and reliable process to seal lancets for storing them in an efficient manner and to allow an automatic opening of the magazine so that the lancets can be easily handled by the lancing device without the need of user interaction.

To overcome the negative aspects related to the processes known in the prior art a process for manufacturing packaged lancets is described, comprising the steps:
providing a tape comprising a plurality of lancets comprising a lancet tip and a lancet body enveloping at least the lancet tip with at least one foil, whereby the at least one foil builds a first and a second portion that overlap at least partly and sealing the at least one foil preferably with a laser beam at least at the edges of the first and second portion of the overlapping parts.

The process describes a manufacturing process for lancets which are packaged for example in a blister pack. The lancets can be used in a lancing device having a drive unit which can be automatically coupled to a lancet in a magazine to accelerate the lancet for executing a pricking process. Such lancing devices are normally used in a hospital or by a patient himself who samples blood several times during a day to measure an analyte for example blood glucose with a home monitoring system. For a convenient handling of the lancing device it is advantageous to store several lancets in the system so that the user has not to change manually the lancet after the pricking step. Therefore, a plurality of lancets are normally stored within a magazine of a modern lancing system and are handled automatically by the system itself. In particular a lancet is automatically coupled to a drive unit of a lancing device and is driven out of the magazine to execute a pricking step. Afterwards the lancet is preferably re-magazinated within the housing of the device and the lancet then is decoupled from the drive unit so that a new lancet can be connected thereto if the patient executes the next pricking process. The automatic handling also includes a removal of the sterile packaging so that in particular the needle tip is released from the sterile cover. However, to avoid contaminations or infections the lancets have to be stored in a sterile environment after the manufacturing process of the lancet magazine until the lancet will be used by a patient. That means that the magazine in which a plurality of lancets are stored must be suitable to keep the environment of the lancet sterile over a long period of time, for example several years. Therefore the packaging has to fulfill specific requirements in particular with respect to the material of which the sterile cover is made as well as the manufacturing process during which the cover has to be sealed accordingly. As a consequence metal foils are for example used to seal the lancet in an airtight environment. However, for an automatic removal of the sterile cover the needle is often simply driven through the foil as described in the prior art and is then damaged by a metal foil but even if plastic foils are used for example in a blister pack as it is described for example in DE 2803345. Such blister packs are manufactured by assembling two foils together and sealing this foils by a hot melting process. As a consequence the needle is surrounded by a welding seam. If the needle is then pushed through the foils the needle has to be driven through the welding seam, whereby the needle tip can be damaged although a soft plastic foil is used.

The prior art systems alternatively, comprise a cap removing mechanism which removes the cap before the pricking step is executed. Such mechanisms unfortunately are normally complex so that a compact and small lancing device cannot be realized.

Inventively the claimed manufacturing process does not use two separate foils which are assembled together so that a welding seam surrounds the needle as realized in the prior art systems. In contrast to the prior art the inventive process uses a foil which is folded around the needle tip so that a first and second portion of the foil overlaps at least partially in the area of the lancet tip. In particular the sealing process is not applied to this end of the foil where the lancet tip is located. That means that the area of the foil through which the needle is pushed during a pricking process does not have a welding seam. Therefore the needle tip has not to be driven through a welding seam and damages can be avoided. After folding the foil around the needle tip the foil can be sealed preferably with a laser beam so that the first and second portion are joined together.

However, it has been shown that the sealing process becomes sometimes critical if the foil is folded as described above. In particular, a loop can be caused by the folding process whereby the portions of the foil are no longer in a close contact. In particular the folding process of the foil bears the risk that cavities still remain at this end where the foil is folded and cavities still remain in the packaging in particular in the welding seam after the sealing process. If so, a sterile environment cannot longer be assured depending on the size of the cavities.

Therefore another aspect of the invention is an improvement of the process as described above by providing a tape comprising a plurality of lancets comprising a lancet tip and a lancet body whereby at least the lancet tip is enveloped by at least one foil, and the at least one foil builds a first and a second portion that overlap at least partly and applying a force to the foil in such a way that the foil is pressed onto the lancet in a first direction and, moreover, at least partially the force is also applied in a second direction perpendicular to the first direction so that the first and second portion of the foil overlap so that at least one portion of the foil is flattened towards the end of the lancet opposite to the lancet tip and sealing the at least one foil preferably with a laser beam at least at the edges of the first and second portion of the overlapping parts.

Consequently a force is applied to the foil before the portions of the foils are sealed together. On the one hand the force presses the foil onto the lancet, so that the parts of the foil come in close contact to each other. On the other hand the force also acts in a direction perpendicular thereto to flatten the foil and to stretch the foil towards the rear end of the lancet opposite to a lancet tip. As a consequence the parts of the foils can be joined together without a loop in particular in this area where the foil is folded around the lancet tip. Preferably this is realized by a contactless process for example with air pressure which is directed onto the foil in a direction between 0-90° so that the force can be applied onto the foil directly as well as in a direction perpendicular thereto. In a preferred embodiment air nozzles are used which are adjustable at a specific angle relatively to the foil. Moreover, the pressure of the air can be regulated and is preferably adjustable as a function of the angle setting. Nevertheless, other processes to apply the force to the foil are also considerable. For example mechanical means to push or draw the foil to the rear end of the needle opposite to the needle tip as well known in the prior art can be also used.

Another aspect of the invention is an exact positioning of the lancet relatively to the foil so that the position of the lancet within the packaging is reproducible.

A process for manufacturing packaged lancets, comprising the steps of providing a metal sheet comprising a plurality of lancets which are fixed to the metal sheet via at least one predetermined breaking points whereby the lancets comprise a lancet tip and a lancet body. Positioning the metal sheet relatively to a tape comprising at least one foil for enveloping at least the lancet tip and placing at least one lancet onto the tape and pressing the at least one lancet onto the tape so that the at least one breaking point is broken and the lancet is not longer connected with the metal sheet. Before, simultaneously or afterwards fixing the lancet on the tape removing the metal sheet and enveloping at least the lancet tip with the foil, whereby the foil builds a first and a second portion that overlap at least partly, sealing the at least one foil preferably with a laser beam at least at the edges of the first and second portion of the overlapping parts.

An exact positioning of the lancet is for example important if the lancets are used in a lancing device as described above. In particular the lancets have to be positioned in a magazine in a defined way relatively to a drive unit of a lancing device so that a coupling element which connects the lancet with the drive unit can be exactly coupled to the lancet in a well defined and a reproducible manner. As a consequence the position of the lancet within the system can be exactly determined and an exact regulation of the pricking depth is possible to ensure a painless pricking process. Therefore a reproducible positioning of the lancet within the foil has to be ensured also during the manufacturing process. That means that a lancet which is normally not longer than 1 cm has to be handled in an exact way during a mass production process. Inventively the problem is solved by providing a metal sheet comprising a lancet structure. Preferably the lancet structure is produced by an etching process which can be easily realized with low tolerances. Of course other processes to cut out a lancet structure in a metal sheet are also possible. For example a cutting process by a laser is also applicable or other processes as well known in the prior art. The lancet structure however is not completely cut out of the metal sheet but is still connected with the metal sheet via predetermined breaking points so that the lancets are still positioned in a defined way relatively to the dimension of the metal sheet. Therefore, not a single lancet has to be handled and to be positioned on a foil but a continuous metal sheet which has now to be positioned in a defined way relatively to a tape for enveloping at least the lancet tip. As well known by a skilled person an exact position of two tapes can be easily realized also in a mass production process. The metal sheet is then placed on the tape which is preferably a plastic foil for enveloping at least the lancet tip. At this time the lancet is still connected to the metal sheet which is now placed on the plastic foil and the lancet is then pressed downwardly onto the tape and thereby is fixed to the tape for example by an hot melting process. Simultaneously, before or afterwards the lancet is disconnected from the metal sheet by breaking the predetermined breaking point. After the lancets are fixed on the tape and disconnected from the metal sheet the metal sheet then can be removed. Afterwards at least the tip of the lancet is enveloped by building a first and second portion of the tape that overlap at least partially. Lastly the foil is sealed at the edges of the first and the second portion of the overlapping parts so that the lancet can be sealed in a sterile environment. Preferably a force is therefore applied to the foil before the edges of the foil are sealed so that the foil is flatten towards the rear end of the needle opposite the needle tip so that the first and second portion of the foils overlap and come in a close contact with each other as described above. The first and second portion of the foil are now sealed in an air tight manner which fulfills the requirement for a sterile packaging of lancets. Moreover, in an advantageous process a laser beam is used for the sealing step.

The process of sealing at least one foil surrounding at least a tip of a lancet with preferably a laser is also a contact-less process. Even complex three dimensional objects may be sealed by this process. Examples of these objects are lancets which are surrounded by a foil. As no further material is brought into contact with the materials surrounding the lancet, no contamination of the foil or the lancet arises. In contrast if the laser application to the foils and substrates is used during the laser sealing process guarantees even a sterile surrounding of the surfaces contacted by the laser. When the laser is focused on the overlapping part of the at least one foil, a sealing line is built between the two layers of foil(s). With the laser sealing process the dimension of the sealing line is diminished compared to other sealing techniques because the expansion of a laser beam is very small (in the dimension of light wavelength). Even if the sealing process of the foil is established with a laminar laser sealing process the dimension of the sealing line is much smaller than that of a sealing processed by adhesive or heat sealing described in the prior art. A further advantage of the laser sealing process is the guarantee that the foils are sealed in an air tight way. This guarantee is reached by a sufficient energy input of the laser to the foil, which melts the foil homogeneously and in a reproducible manner. Nevertheless, other sealing processes as known in the prior art are also possible as for example heat melting process. However, it has been shown that the laser sealing process is in particular advantageous in combination with the inventive process. For example the laser sealing process can easily be controlled. There are at least 3 parameters which have to be controlled:

laser power focused on a certain area
homogenity of the foil
closeness of the foils at the sealing place In the laser sealing process, materials might be used as foil, which are meltable by the laser in a way that the foil is melted by the laser and this melting process results in gluing of the 2 foil layers without cutting or destroying the foil. Some substances to be used as foil material might be for example a PET (polyester) foil, PP (polypropylene), PE (polyethylene), cyclic polyolefines (e.g. TOPAS®), PVAC (polyvinylacetate), PMMA (polymethylmethacrylate) or PA (polyamide). There is no limitation of foil material to be utilized in this process despite the fact that it has to be meltable by the energy of the laser, without being destroyed by this process.

It is possible to use different materials for the first and second portion of the foil. At least one material has to be meltable by the light of a laser. The other portion should interact with the melted portion in a way, that a stable interaction of the two portions is reached. In a preferred embodiment both portions consist of the same material.

In case the two portions belong to one foil the third portion is also part of the foil. In this preferred embodiment the third portion builds the edge between the overlapping first and second portion built by the foil. If only one foil is used to surround the lancet the process may be established in a very time and material effective way. The process with only one foil comprises one step less than a process where two different foils are used. The surrounding of the lancet with only one foil can be established much easier than with more than one foil because only one feeding mechanism has to be operated and the alignment of the foil with the lancet has only to be established once.

The process of sealing the at least one foil at least at the edges of the first and second portion of the overlapping parts may be established with different kinds of lasers. The energy of the laser beam has to be adapted to the melting properties of the at least one foil. Examples of a laser are:
a) Nd:YAG;
b) $CO_2$;
c) diode laser
d) fiber laser These lasers have different properties which can be used for different purposes in this sealing and cutting process. The Nd:YAG laser has a high beam quality because of a high stability, small laser spot (about 10-50 μm) and might be conducted through a fibre optic cable. This laser might be used in a continuous as well as a batch mode, where a power of 20-600 W is normally used in continuous methods, but the laser is also able to beam with a power of 5 kW.

The CO2 laser has a less quality because the laser spot can be focused to about 150-350 μm. Therefore this laser is much cheaper. It also can be used in continuous mode especially for the melting of polymers in the power range of 10-600 W, up to 5 kW. The beam is normally focused onto the substrate via a mirror optic.

The diode laser has the advantage to be built and integrated in a very scaled system because of its small dimensions (several centimetres). The laser diode builds an efficient beam source in the infrared region, where its efficiency is about 50%. One laser diode might reach about 100 W power, but may be coupled with other diodes to reach the kilowatt region.

At least the tip of the lancet is surrounded by the at least one foil. During the sealing process the laser beam is conducted at least across the edges of overlapping parts of the at least one foil. The shape of the overlapping at least one foil is not limited. The overlapping foil may be in the form of a circle, a triangle, a square or a rectangle as well as oval and combinations thereof. In a preferred embodiment the shape of the foil is rectangular. The dimension of the first and second portions of the foil(s) might be identical, but also might differ in size. In a preferred embodiment the dimensions of first and second portion are identical.

As the dimension of the sealing line is very small, it is possible to encapsulate the lancet at least in the region of the lancet tip in a very space reduced way. The result is a space and material effective process and leads to a possibility to store many lancets in a small storing facility.

In another preferred embodiment the lancet is sealed between the two portions of at least one foil together with its lancet body. Before the lancets are positioned in or onto the tape, the lancet body may be at least partially covered by meltable glue. By this meltable glue the lancet may be fixed to the substrate or tape at least partially. With this fixing an unwanted destruction of the foil before use of the lancet may be avoided. In this embodiment the lancet tip may be movable in the sealed surrounding in a stored form without the risk of destroying the foil by accident.

In the combination of the lancet with a pricking device the lancet might be used to pierce or prick the skin of a patient with the aim of generating body fluid. The body fluid may be collected in the form of interstitial fluid, serum, plasma or whole blood. During the use of the lancet in a pricking device, at least the lancet tip is forced through the foil. As the foil has a very small thickness the lancet tip won't be unsharpened or contaminated by cutting the foil. After generating a sample of body fluid the sample might be transferred to a test element which incorporates reagents able to react with an analyte in the sample. This analyte might be any molecule in the sample, like e.g. glucose, cholesterol or other substances in the fluid.

The pricking device and/or the test element might be part of a meter which is able to analyse the test element to generate a result for the concentration of the analyte. This might be an optical, electrochemical, amperometric, potentiometric or any other detection method known in the prior art for detection of analytes in body fluids.

The pricking devices, test elements and meters are well known in the prior art and don't have to be explained in detail for a person skilled in the art. Examples are found in U.S. Pat. No. 5,879,311; U.S. Pat. No. 6,866,675 and U.S. Pat. No. 5,857,983 for pricking devices; U.S. Pat. No. 4,999,582; U.S. Pat. No. 6,506,575; U.S. Pat. No. 6,036,919 and EP 0230472 for test elements or EP 591226 for meters. Lancets and the procedure of their production are known for example from EP0565970.

It depends on the melting point and the thickness of the at least one foil, which energy input is necessary to melt the foil sufficiently in a short time range of milliseconds. The thickness of the foils may be in the range of 1 μm to 100 μm preferentially in the range of 5 µm to 30 µm and most preferably about 10 µm. This process might be established with a speed of about 5 meters/minute. During the process of covering the lancet and/or substrate by the foil(s) the foil may be bent in one or two dimensions of the foil layer. With this bending of the foil a pre-stressed cover of the lancet is reached that can easily be destroyed by the lancet during the lancing process. By the pre-stressed status of the foil the cut edges of the foil will move away from the lancet tip during and after the cutting process so less contamination with any material of the lancet may be reached with this pre-stressing.

During the sealing process the first and second portion of the overlapping at least one foil should be very near to each other preferably contact each other at least at the parts where they should be sealed together. The foils may be kept near the substrate by adhesion forces. These adhesion forces may be varied by the choice of material. These adhesion forces are the result of the surface properties of the foils. Material that might be loaded electro-statically enlarges the adhesion forces. The procedures to load electro-static forces onto the surface of materials are well known in the prior art. These adhesion forces may be of the strength that the substrate is covered air-tight to the foil. These adhesion forces might also be generated between the two portions of the foil covering the lancet placed in or on the substrate or tape.

Another option to bring the foil(s) air-tight around the lancet and/or substrate is the application of a vacuum or pressure during the process of covering the foil around the lancet and/or substrate. By this process the foil portions are laminated to one another. This may also be reached by rolls where the foil is lead through together with the lancet and the substrate.

With this optimized process at least parts of the first and second portion of the at least one foil are melted by the laser beam during the sealing process. The dimension of the melted parts depends on the broadness of the laser beam and the capacity of the foil to absorb the light energy of the laser. The dimension of the melting line may range from 0.05 mm to several millimetres.

During the process the at last one foil may be cut by the sealing process. The sealing process can also be used to singularize the lancets if they are produced for example in a web like manner by etching or other techniques. As example for a continuous process the laser power of for example a laser diode (940 nm), with a used spot range of 3 mm might be 20 W. This might be varied in a wide range depending on the used material and the speed of the process.

An example of a web might be a flat steel foil into which at least the lancet tips are etched or stamped. This steel foil might have a thickness of between 0.07 and 1 mm. The lancet tips might be sealed by the foil before, after or even during the singularization step. This depends on the aim of the laser processing. If the web should be used as magazination form, where the lancets are not singularized before use or where the singularization step is not established by the laser then the energy of the laser is adapted to just melt at least one foil without cutting it.

In a preferred embodiment the sealing of the lancet tip and the singularization is done in one process step with the laser. Here the laser energy has to be higher because the web, for example the steel foil, has to be cut in this process beyond the sealing of the foil.

In one embodiment one foil covers a first side of the lancet, building the first portion and a second foil covers a second side of the lancet, building the second portion. These two foils may comprise the same ingredients or may be composed by different materials.

In another embodiment at least one of the two portions of the at least one foil also covers the body of the lancet.

The body of the at least one lancet may be affixed to the foil. This affixing may be performed by a laser or another heat source like a hot stamp.

The heating of the foil on the lancet body results in a fixation of the foil onto the lancet body, because the foil melts even in small parts while contacting the lancet body. In this embodiment the materials of the foil and the lancet body might be chosen in a way that they bond to each other when the foil is melted. During this process the lancet body preferably does not melt by the heat applied.

In another embodiment a first portion of the foil covers a first side of the lancet and a second portion covers a second side of the lancet wherein the first and second portion are connected by a third portion which is located in front of the lancet tip. These three portions may belong to one foil which overlaps at least a part of the lancet. The first and second portion may cover each one different side of the length of the lancet and the third portion combines these two portions by surrounding the lancet tip. The material and/or the thickness of the foil portions may vary in these 3 portions, but preferably the materials of the three foil portions are the same and even the thickness may be the same.

The sealing of the foil may be established with a laminar laser sealing process. In this laminar laser sealing process a laser sealing is achieved which has a broader sealing line than the sealing with a very focused laser process. The laminar laser sealing process is normally established with a $CO_2$ laser or a diode laser.

The lancet may be of any material like metal or mixtures of metals, polymers, ceramics or any other stable material from which a sharp lancet tip may be built which is strong enough to enter the skin of a patient without deforming, being bent or destroyed. If the lancets are fabricated e.g. in the form of a metallic web or tape where the lancet tips are formed in an etching process the plurality of lancets may be separated by the laser beam during the sealing process. Within this process the power of the laser has to be high enough to cut a metal sheet in a range of 0.07-1 mm. While the metal is cut also the foil layers are cut and the foil is fixed to the metal edges of the lancet body by this process.

During or before the sealing and/or cutting process the plurality of lancets may be placed on a substrate. The material of the substrate may vary. It may be another foil or a web of different fabrics like polyester, polypropylene, polyethylene, cyclic polyolefines (e.g. TOPAS®), polymethylmethacrylate, polyvinylacetate or polyamide. Examples of different materials are given in the US 20050245845. For magazination purposes the plurality of lancets may be fixed on a tape which is flexible enough to wind the tape on roles or coils.

The lancets may be stored in different ways after their singularization. In one embodiment they are placed on a web whereby each lancet can be actuated separately. The lancet may be combined with a test element before placing the lancet on the web or afterwards. In another embodiment test elements may be placed in between the lancets.

A different form of storing the singularized lancets is for example a stack magazination. Other forms of storing the lancets or the lancet integrated test elements are possible as well. There are several alternatives which are well known in the prior art.

After or during the cutting and/or sealing process the lancets may be sterilized. This sterilization may be established for example by heat or by radiation or other known sterilization procedures.

Additionally the lancet body may be attached to a test element. This test element preferably has a testing field onto which fluid samples like blood are applied. In combination with the lancet this test element may be brought into direct contact with the pierced tissue where blood can be taken up by the test field. An example of a lancet coupled to a test element is shown in US-20060079810. Another possibility to combine a test element and a lancet is described in the U.S. Pat. No. 6,866,675. Here the lancet additionally incorporates a capillary channel or a different structure to collect a body fluid after being pierced into the skin of a patient. This blood may then be transferred to a test element that is positioned in direct contact to the capillary channel or may be stored separately.

The test field may incorporate chemicals like enzymes which interact with the analyte of the sample to measure the concentration of the analyte.

The described invention also covers a device for collecting body fluid, comprising:

a. a lancet, with a lancet tip and a lancet body, and
b. at least one foil, that envelopes at least the tip of the lancet whereby the at least one foil builds a first and a second portion that overlap each other at least partly,
wherein the foil is sealed after enveloping at least a part of the lancet by treating at least the edges built by the two partly overlapping portions of the at least one foil with a laser to keep at least the lancet tip in a hermetic surrounding.

This device may be processed by the process described before.

When the device is attached to a further test element at least the lancet may be movable in the foil. This allows a separate movement of the lancet in relation to the test element and in relation to the foil. To move the lancet through the foil, the device with the test element and/or the lancet may be placed in a meter which may incorporate a lancet actuator. Furthermore the meter may incorporate a test element actuator which may be the same as the lancet actuator and additionally may comprise a reading facility to read out the test element. This read out may deliver different results, depending on the specification of the test element.

Examples of production processes with laser sealing are as follows:

Production Process of a Lancet Label Masters:

A PET (Polyethylenetelephthalate) foil with a thickness of 19 µm (Melinex S® by DuPont) builds the substrate in form of a tape. The surface of the foil is coated by a doctor blade for example in a laminator with a mixture of 20 g Vinnapas B500/20VL® (by Wacker AG Burghausen) in toluene. The gap of the doctor blade is about 120 µm, the velocity of the tape is 0.5 m/min. Drying of the coating is performed with warm air of about 50° C. The thickness of the coating after drying is about 12 µm. The Vinnapas coating acts as a hot melt in following steps.

Flat lancets from stainless steel 304® with a thickness of 76 µm and a width of 2.25 mm and a length of 4.56 mm which are produced by etching are exactly positioned in predefined distances onto the coated surface of the PET tape and fixed to the tape by heating just the lancet body with a hot stamp or laser pulse in order to activate the hotmelt coating.

A bi-directionally stretched PET foil (Hostaphan RN® by Mitsubishi Polyester Film, Wiesbaden) with a thickness of 6 µm is smoothly applied to the lancet tape by using a soft roll. The excess parts of the foil are cut at the edges of the tape by a $CO_2$ laser Starshape 300 C® (by Ronin). The adjustments of the laser are: 200 mm lens, velocity of the mirror 1000 mm/sec, power 120 parts=31 J/m. The cutting width is about 300 µm.

The so bonded tape is laminated with its down side onto a DuroTak® type 387-2825/87-285 (by National Starch B.V.) transfer adhesive foil. This adhesive transfer foil consists of a release-liner and a film of 20 µm glue. After lamination the tape is rolled up on a roll and sterilized by for example radiation.

Production Process of Lancet Labels from the Master:

By a $CO_2$ laser Starshape 300C® (by Ronin) lancet labels are cut from the tape. Each label may comprise one, two or three lancets in a row. The distance of the broadest part of the lancet to the cutting line is at least 0.5 mm. The width of the label is at least 1 mm wider than the length of the lancet. The rest material which does not belong to the labels is eliminated. It results a liner with self-adhesive lancet labels.

Production Process of a Lancet Tape:

The transport foil of the resulting lancet tape is a bi-directionally stretched PET foil (Hostaphan RN® by Mitsubishi Polyester Film, Wiesbaden) with a thickness of 12 µm. Single lancet labels are transferred to this PET transport foil by positioning exactly on the foil. The accuracy of this transfer is at least +/−1/10 mm. This lancet tape will be cut by a $CO_2$ laser Starshape 300C® (by Ronin) into three lancet tapes with a width of 5.0 mm. The end of the lancet body is positioned about 0.2 mm from the cutting edge.

With these processes a very fast sealing may be achieved with a very precise and reproducible sealing result. The quality of the sealing process is more precise and more reproducible as the processes of hot gluing and hot stamping.

DESCRIPTION OF THE SELECTED EMBODIMENTS

Figures 1, 2A, 2B:
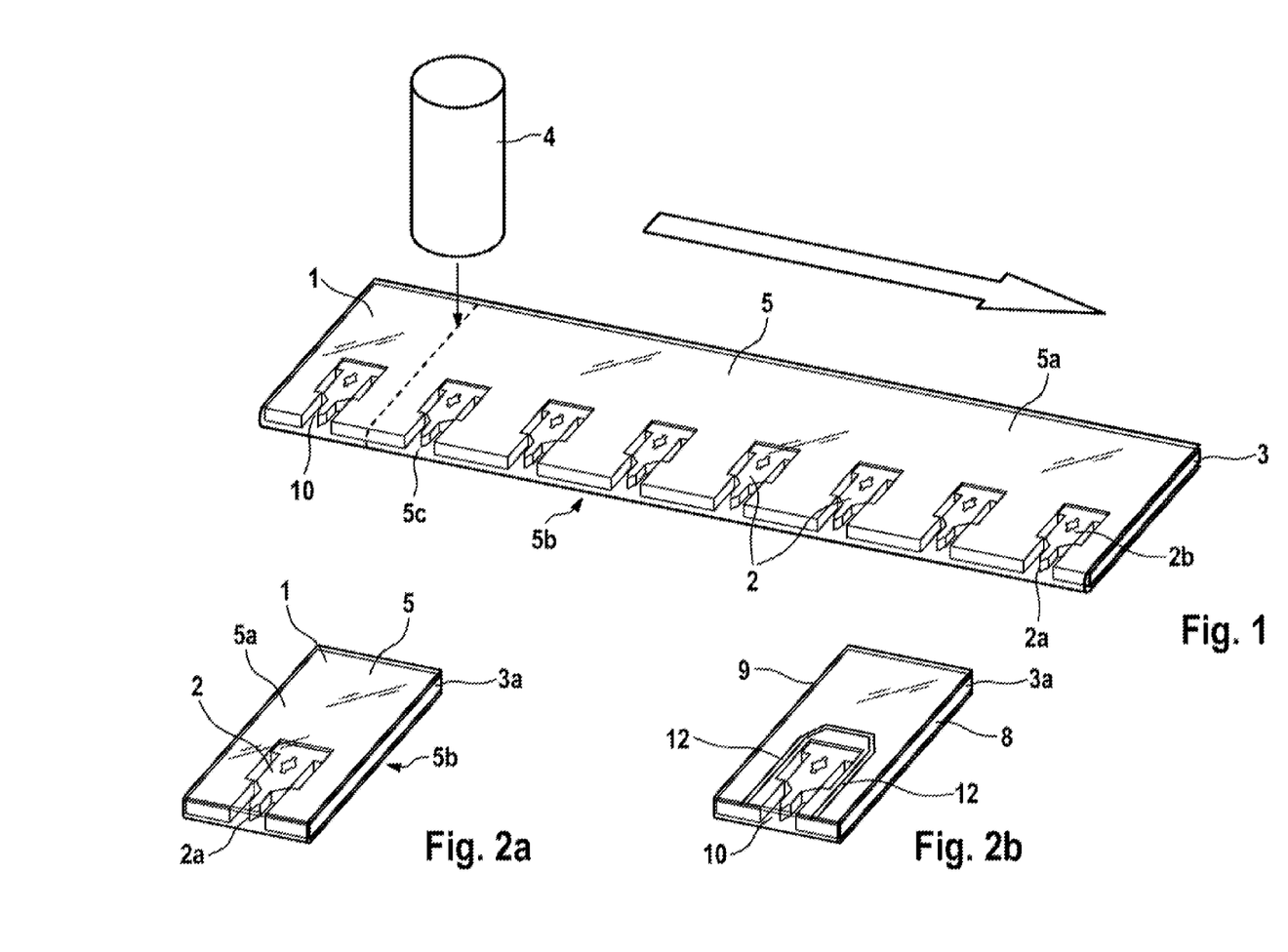
FIG. 1 is a perspective view of a lancet magazination with a foil surrounding at least the tips of the lancets.
FIGS. 2a and 2b show a sealed lancet cut by a laser where all edges are sealed by the laser cut.

In FIG. 1 a lancet tape (3) is shown where a plurality of lancets (2) are positioned on or are part of the lancet tape (3). Preferably the lancets (2) are all positioned in the same direction on or in the tape (3). The lancet tips (2a) of the lancets (2) should be reachable from at least one side of the tape (3). This lancet tape (3) is covered by a foil (5) which overlaps next to the lancet tip (2a) on both sides of the tape. On one side of the lancet tape (3) this foil (5) builds the first portion (5 a) of the foil. On the opposite side of the lancet tape (3) the second portion (5b) of the foil (5) is placed. When the lancet tape (3) is covered by only one foil (5) this foil (5) builds a third portion (5c) which is built by the overlaps of the foil (5) at least in the region of the lancets tip (2a) at one edge of the lancet tape (3). If the two portions (5a) and (5b) of the foil (5) are built by two separate foils, the third portion (5c) is built by the overlapping parts of the two foils which extend beyond the substrate (3a). When the two foils are melted together in the sealing process in form of the sealing line this third portion (5c) is formed. During the sealing process of the labels (1) where two foils are used, the overlapping parts of the foils beyond the substrate (3a) are cut during the sealing process or the cutting process or the combined sealing and cutting process. In between the overlapping portions (5a) and (5b) of the foil (5) at least the tip (2a) of the lancet (2) is positioned. In the shown embodiment the whole lancet (2) is covered by the first portion (5a) and the second portion (5b) of the foil (5).

The lancets (2) can be singularized from this lancet tape (3) in form of a lancet label (1) by cutting the lancet tape (3) with a laser (4). After overlapping at least the lancet tip (2a) with the at least one foil the three portions (5a), (5b) and (5c) of the foil are laser sealed together by a $CO_2$ or Nd:YAG laser. After this sealing process at least the lancet tip (2a) is sealed by the foil portions (5a, 5b, 5c).

In FIG. 2 a lancet label (1) is shown which incorporates a part of the lancet tape (3) in form of a substrate (3a). In or on this substrate (3a) the lancet (2) is positioned. In this case the form of the lancet label (1) is rectangular, but there is no limitation of the geometry of this lancet label (1). It also could have a round or a oval form. During the singularization process the laser (4) cuts the foil (5) together with the substrate (3a) of the lancet tape (3). The foil is melted by this process and sticks onto the substrate (3a) so that the lancet label (1) is sealed at the cutting edges (8) and (9). The lancet (2) is surrounded by the three portions (5a), (5b) and (5c) in a sealed manner. A process that is not shown in FIGS. 1 and 2 is the sealing of the lancet (2) in its cavity (10) which is build into the substrate (3a) of the lancet tape (3) when the lancets (2) are positioned in the lancet tape (3). These cavities (10) are built into the lancet tape (3) by a cut so that a lancet (2) may be positioned into this cavity before the lancet labels (1) are formed by the laser cutting process. During or before the cutting process shown in FIG. 1 the cavities (10) are sealed by the laser (4) whereby the laser beam (4) surrounds the cavities (10) where the lancets (2) are placed in. By this process the foil (5) is melted to the substrate (3a) so that the lancet (2) can be kept sterile in its cavity (10). For this sealing process the laser power of the laser (4) is less than for the cutting process shown in FIG. 1. After the sealing process at least the lancet (2) is surrounded by the three portions (5a, 5b, 5c) of the foil (5). The sealing line (12) may be adjusted to the geometry of the cavity (10). This sealing process may be checked by optical or pyrometric processes. This may be executed by e.g. a CCD-camera, a thermo camera or pyrometers).

Figure 3:
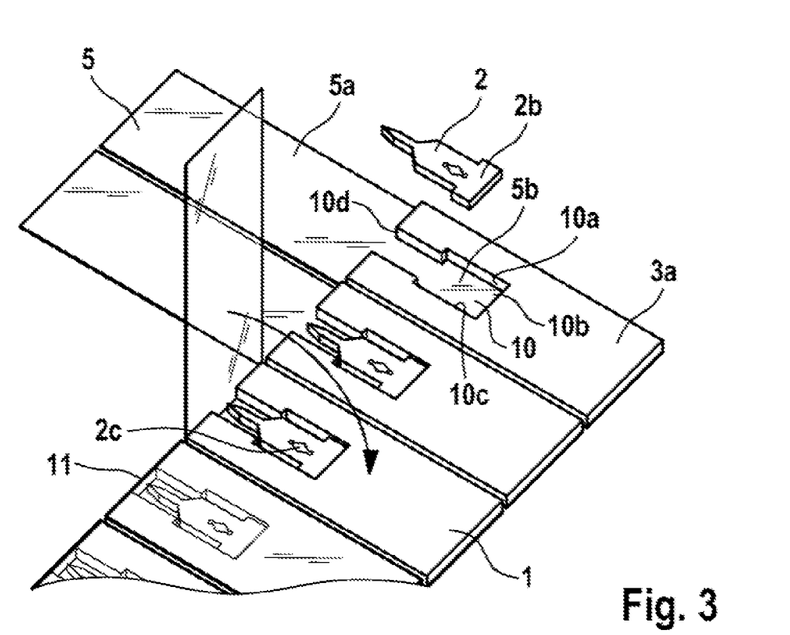
FIGS. 3 and 3a show a lancet in or on a substrate which are surrounded by the sealing foil whereby the foil is bond to the substrate by a laser welding.
Figure 3A:
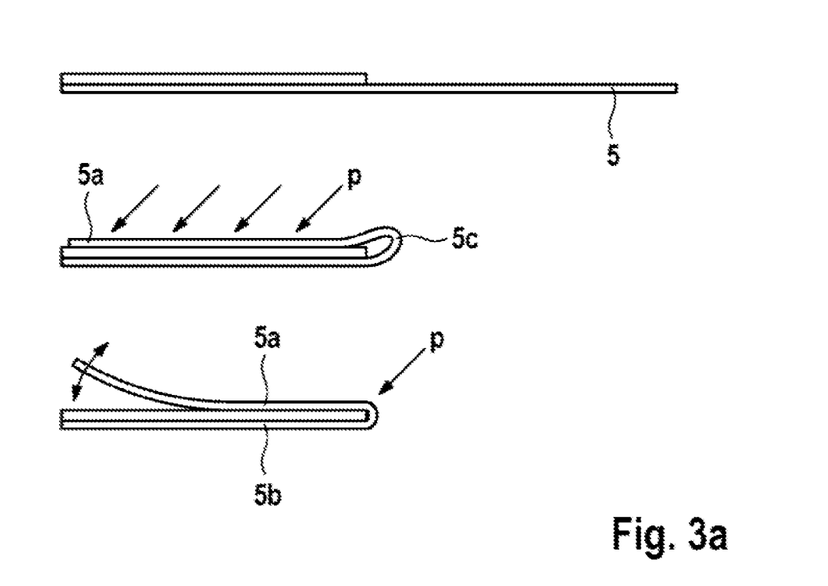
Figure 4:
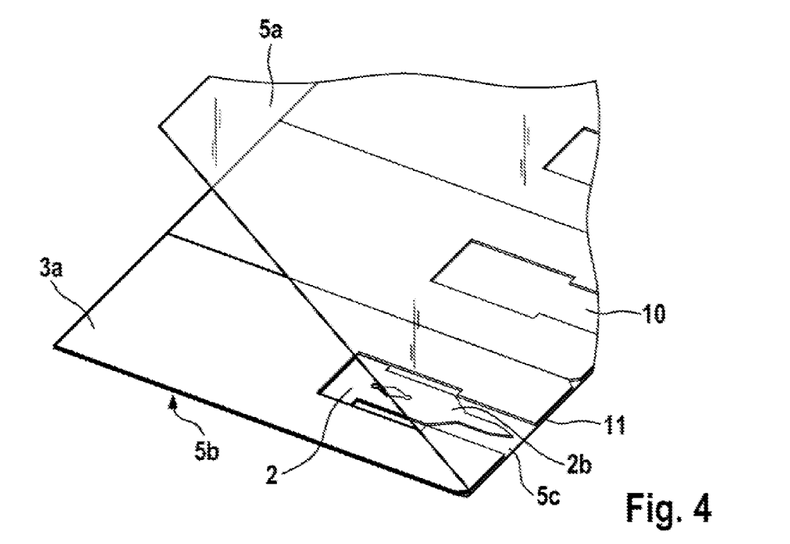
FIGS. 4, 4a, and 4b show a substrate in form of a tape is shown where a plurality of lancets is placed in or on, which is at least partially overlapped by a sealing foil.

In FIGS. 3, 3a and 4 two different processes are shown to cover the lancet label (1) or the lancet tape (3) with the foil (5). In FIG. 3 each lancet label (1) is already cut and singularized. The cut lancet label (1) is positioned onto the foil (5) whereby the cavity (10) is filled with the lancet (2) before the foil (5) is folded across the front edge (11) of the label (1). The foil 5 is then folded in such a way that the foil portion 5a and 5b overlap. As it is shown in FIG. 3a a loop (5c) is resulted from the folding process in this area where the foil is folded and which surrounds the lancet tip. To avoid such a loop a air pressure (P) is applied against the foil so that the foil is pressed onto the lancet label (1) and moreover the force also is applied in a direction perpendicular thereto so that the foil is flattened towards the rear end of the lancet body and is closely aligned with the lancet label. In particular the force is applied in a defined angle (a) relatively to the tape. The foil is then fixed to the substrate (3a) e.g. by laser welding. Because of the small dimension of the laser even in the welding process, the lancet is not involved in this welding process. So the lancet is not fixed by this welding process. After this welding process the foil (5) may be sealed at least at the edge (10d) resulting in a lancet tip (2a) which is kept sterile by sealing the cavity (10) by laser sealing. This welding and sealing process may be performed by a diode laser with a wavelength of 940 nm. Moreover, the lancet body but preferably not the lancet tip can be also fixed to the tape by an additional step of the welding process as well known in the prior art.

In a preferred sealing process the cavity (10) is additionally sealed at its edges (10a, 10b, 10c, 10d) around the lancet (2). So the lancet (2) is surrounded by at least 4 sealing lines (not shown), whereby at least one sealing line at the edge (10d) is formed only into the foil portions (5a) and (5b), whereas the other sealing lines at the edges (10a, 10 b, 10c) are formed between the foil (5) and the substrate (3a). Dependent on the position of the sealing line built by the foil portions (5a) and (5b) at the edge (10d) a small channel might be built out of parts of the first (5a) and second portions (5b) together with the third portion (5c) of the foil (5). If the sealing line is not positioned directly on the edge (10d) but closer to the lancet tip (2a) so that first (5a) and second portions (5b) are involved in the sealing line, the sealing line separates the third portion (5c) of the foil (5) from the rest of the foil (5) by building this channel at the edge (10d). This channel guarantees the hermetic separation of the sealed cavity (10) with the lancet (2) inside, after the sealing process of the cavity (10). It is also possible to position the sealing line on the edge (10d) to reach a sealed cavity (10). Here the sealing line only incorporates the third portion of the foil.

The lancet body (2b) may incorporate an element (2c) to cooperate with a system component like an actuation or piercing device. This element (2c) may have different shapes like a hole or cavity, a champ or hook or a guiding member. This element may contact a plunger of the actuation device or meter (not shown in the figures). By this interaction of the lancet (2) and the actuation device the lancet (2) may be moved out of the pocket or cavity (10) by destroying the foil (5) at the third portion (5c) by the lancet tip (2a). By this actuation process of the lancet (2) also parts of the other portions (5a) and (5b) might be destroyed. The destroyed parts of the foil after the actuation of the lancet are preferentially pushed outside of the cavity (10) so the lancet (2) is free of any material when reaching the skin of the user.

Alternatively the foil may be peeled away by for example a gripper in form of for example a tweezers during the use of the lancet (2) in a pricking device (not shown).

In FIG. 4 the surrounding of the lancet tape (3) is shown where the sealing process is established before the cutting process to create separate labels (1). Here an almost continuous foil (5) may be used to cover the two sides of the substrate (3a) and the lancets (2). In FIG. 4 only one foil (5) is used to cover both sides of the substrate (3a) whereby both foil portions (5a) and (5b) run over into the third portion (5c) built by the overlapping parts of the foil (5) at the front edge (11) of the substrate (3a).

Figure 4A:
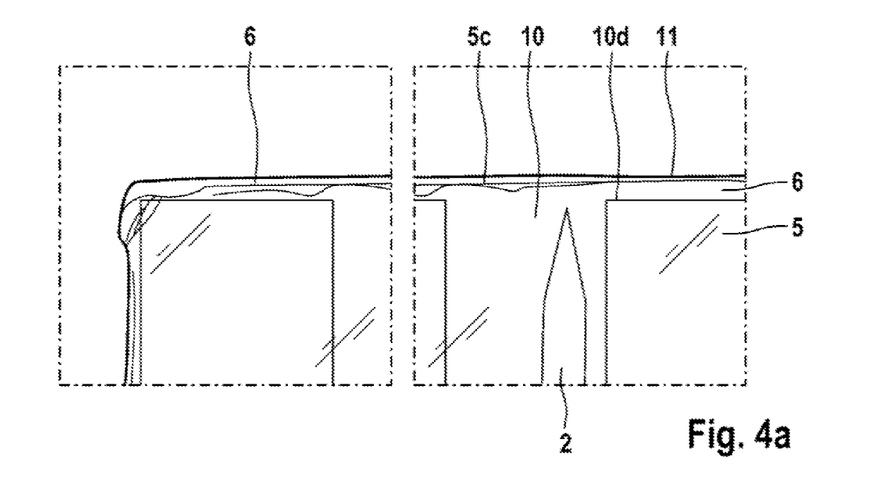

FIG. 4a shows the lancet (2) in its cavity (10) before the sealing process or alternatively after a hot sealing process. In both cases the foil (5) builds an overlapping portion (5c) at the edge (10d) respectively (11) of the substrate (3a). This overlapping part (6) builds a risk to loose the hermetic surrounding of the lancet (2) after the sealing process because the hot sealing process is not able to reach the overlapping part in form of the third portion (5c) in front of the lancet tip (2a).

This is a result of the dimension of the hot sealing stamps which could not be adjusted to such a small dimension as a laser sealing line.

Figure 4B:
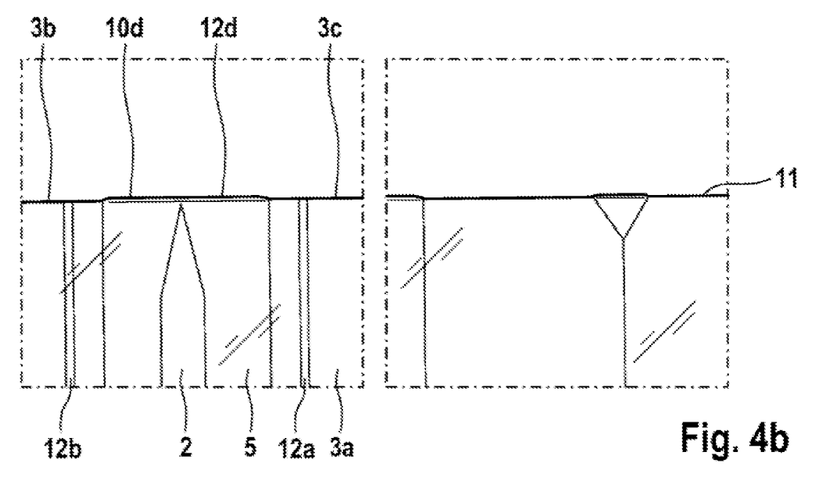

FIG. 4b shows a lancet (2) after the laser sealing process. It can be seen that the foil (5) is welded onto the substrate (3a) without building an overlap at the edge 10d of the substrate (3a). Here the sealing line is identical to the edge (10d) of the substrate (3a). In contrast to this hermetic enclosure of the lancet (2) of FIG. 4a, in FIG. 4b an overlapping part (6) of the foil (5) surrounds the edges (3b) and (3c) of the substrate (3a) when the lancet (2) is sealed by a different sealing process like hot sealing.

Figure 5:
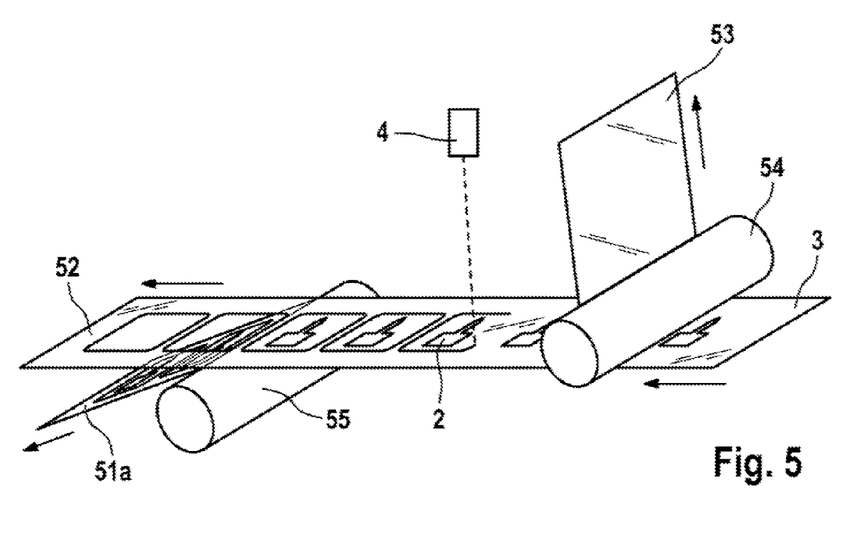
FIGS. 5, 5a, 5b, 5c, and 5d show a process to singularize lancet labels on a tape with a laser.
Figure 5A:
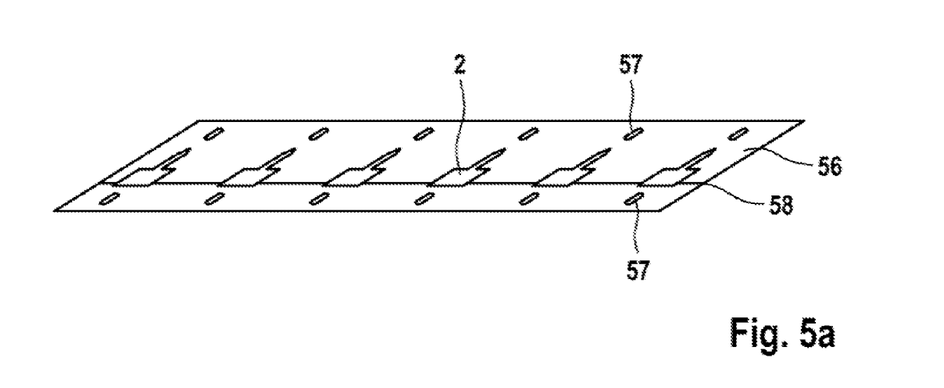
Figure 5B:
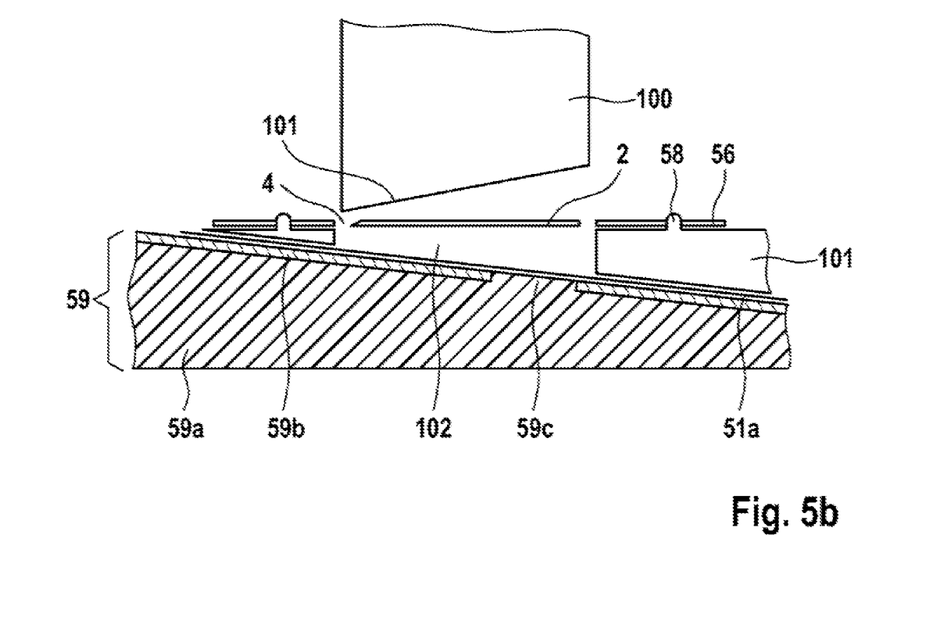
Figure 5C:
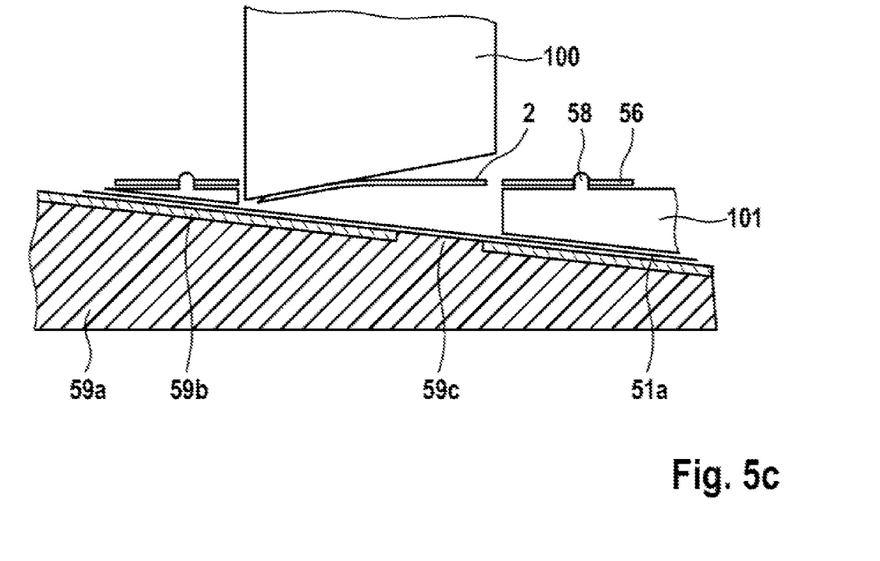
Figure 5D:
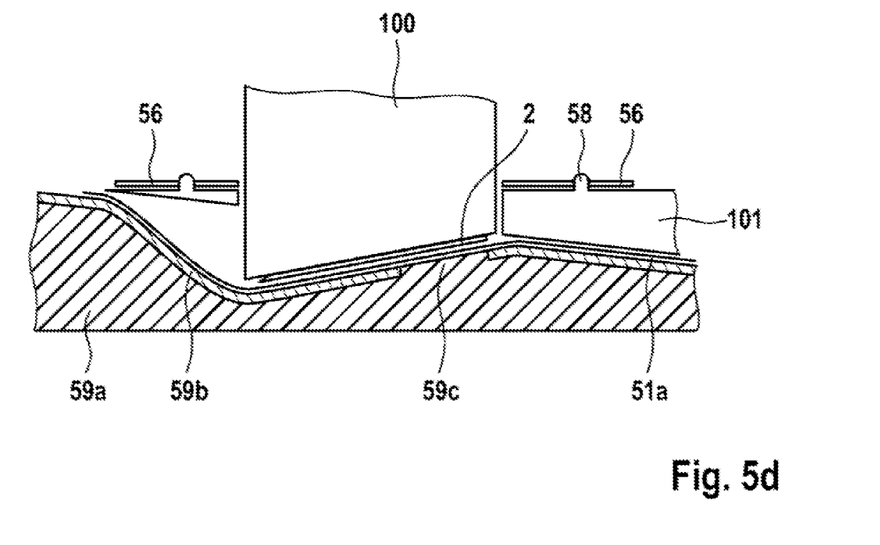

FIGS. 5 and 5a, 5b shows a cutting and sealing process of lancet labels (1) in a continuous process. FIG. 5a shows a metal sheet with a lancet structure which is produced for example by etching process or other processes which are well known in the prior art for example cutting process by laser beam or a stamping process. Moreover in addition to the lancet structure (2) positioning holes (57) are also in the metal sheet which are in a defined position relatively to the lancet. As explained above the lancet are cut out of the metal sheet but are still connected to it by at least one predetermined breaking point (58) for example at the rear end of lancet body. As explained later on this breaking points are broken if the lancets are placed onto a foil to build up a lancet tape 3 as shown in FIG. 5. As shown in FIG. 5b-5d the metal sheet is now placed onto the foil (51 A) to built up a lancet tape (3) as shown in FIG. 5. Advantageously the foil (51 A) is made of plastic for example is a PET foil which is self-adhesive. In particular the foil is positioned under a matrix (101) which comprises pins (58) which are used to position the metal sheet (56) in a defined way relative to the matrix. Therefore the positioning holes (57) of the metal sheet fit into the surface structure of the matrix (101) and allow to position and fix the metal sheet onto the matrix and therefore relatively to the foil (51 A). The matrix moreover has a cut out portion (102) where a lancet is positioned directly within and therefore directly above the plastic foil (51a). A stamp (100) now presses the lancet downwardly onto the plastic foil (51a) as shown in FIGS. 5c and 5d whereby firstly a part of the lancet is only contacted with the plastic foil and is already fixed to it by for example a hot melting process. Simultaneously or afterwards the predetermined breaking points are broken so that the lancets are disconnected from the metal sheet. The stamp (100) has preferably an inclined surface (101) which contacts the lancets so that the lancet tip is firstly contacted with the foil. Afterwards the whole lancet is pressed by the stamp against the foil and is fixed thereto. Preferably the foil (51 A) is placed on a elastic support member (59) so that the pressure which acts on the lancet by the stamp cannot damage the lancet. Such elastic support member can be built from an elastic layer (59 A) which is covered by a thin steel layer (59 B). Preferably the steel layer also has some cut out portions (59c) through which a laser beam can be directed to fix the lancet onto the foil via a hot melting process. Nevertheless, several well known processes are generally possible to fix the lancet on the foil (51 A).

Moreover, it is also possible to keep the lancet temporarily in a defined position on the tape for example by magnet forces and then disconnect the lancet from the metal sheet. Afterwards the lancet can be fixed permanently as described above. Preferably a permanent fixation of the lancet to the tape can be disconnected to execute a pricking process. In particular the connection is automatically broken during the pricking process when the lancet is accelerated by the drive unit. Alternatively the lancet can be still fixed to the tape during the pricking process. In particular the rear end of the lancet body is then still fixed to the tape and the tape can be moved together with the lancet.

Moreover, the lancet tape (3) can be built of at least three layers, a transfer layer (51a), a transport layer (52) and a cover layer (53). These three layers (51a), (52), (53) may all belong of the same material and may be built as foils. These layers may be fixed to each other by an adhesive which sticks the layers together. At least one of the layers builds a foil that covers the lancet (2). The material of the foils may differ or may be the same material. Preferentially the foils belong of the same material. The lancets (2) are incorporated in the transfer layer (51a), whereby the transport layer (52) is positioned at the bottom of the transfer layer (51a) and the cover layer (53) is positioned on top of the transfer layer (51a). The cover layer (53) is removed by a roll (54) directly before the laser cutting and sealing process of the lancets. After the removing of the cover layer (53) the laser (4) cuts lancet labels (1) out of the transport layer (52) whereby parts of the transport layer (52) remain as sealing foil on the transfer layer (51a) and hermetically surrounds the lancets (2). This transfer layer (51a) may now be led to a sterilisation process where the lancets (2) are sterilized and kept sterile because of the sealed lancet label (1).

Figure 6:
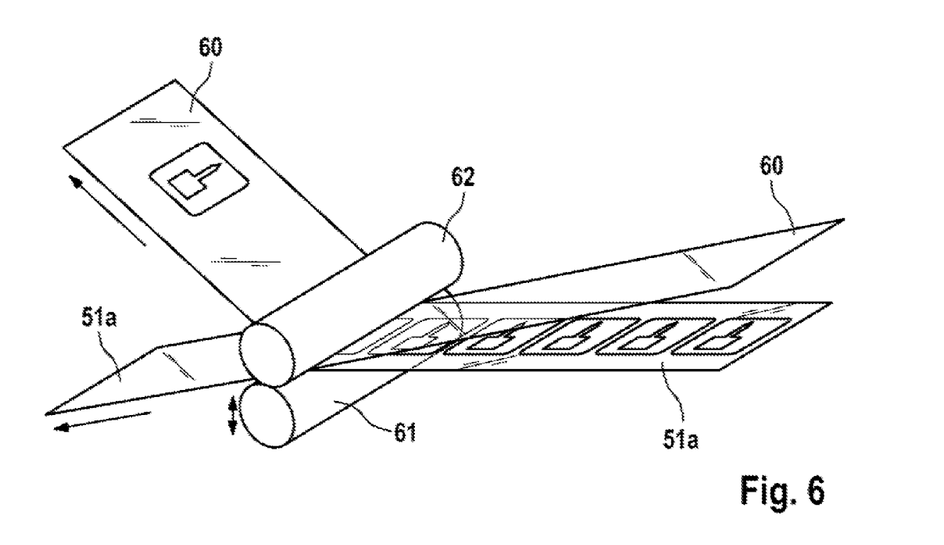
FIG. 6 shows the transfer of singularized lancet labels from the lancet tape to another tape.

These lancet labels (1) may be transferred to another tape (60) by contacting the transfer layer (51a) with the tape (60). This contacting only takes place at a contacting point of the transfer layer (51a) and the tape which are fed in between the two rolls (61) and (62). At the areas where the lancet labels (1) are positioned on the transfer layer (51a) as shown in FIG. 6 the adhesion of the lancet label (1) to the tape (60) is higher than to the transfer layer (51a). To facilitate this transfer process either the tape (60) incorporates sticky regions or the foil on the lancet label (2) is covered by a sticky material or adhesive. This contacting of the tape (60) to the lancet labels (2) is realised by a roller. The roller is built of 2 rolls (61) and (62) which can be pressed against each other in a controlled way. In between these 2 rolls the tape (60) and the transfer layer (51a) are fed. Roll (61) moves the transfer layer (51a) and roll (62) moves the tape (60). By varying the pressure between the two rolls (61) and (62) and by moving the rolls (61) and (62) with different velocities, the place of the transfer of the lancet labels (1) from the transfer layer (51a) to the tape (60) may be varied.

Figure 7:
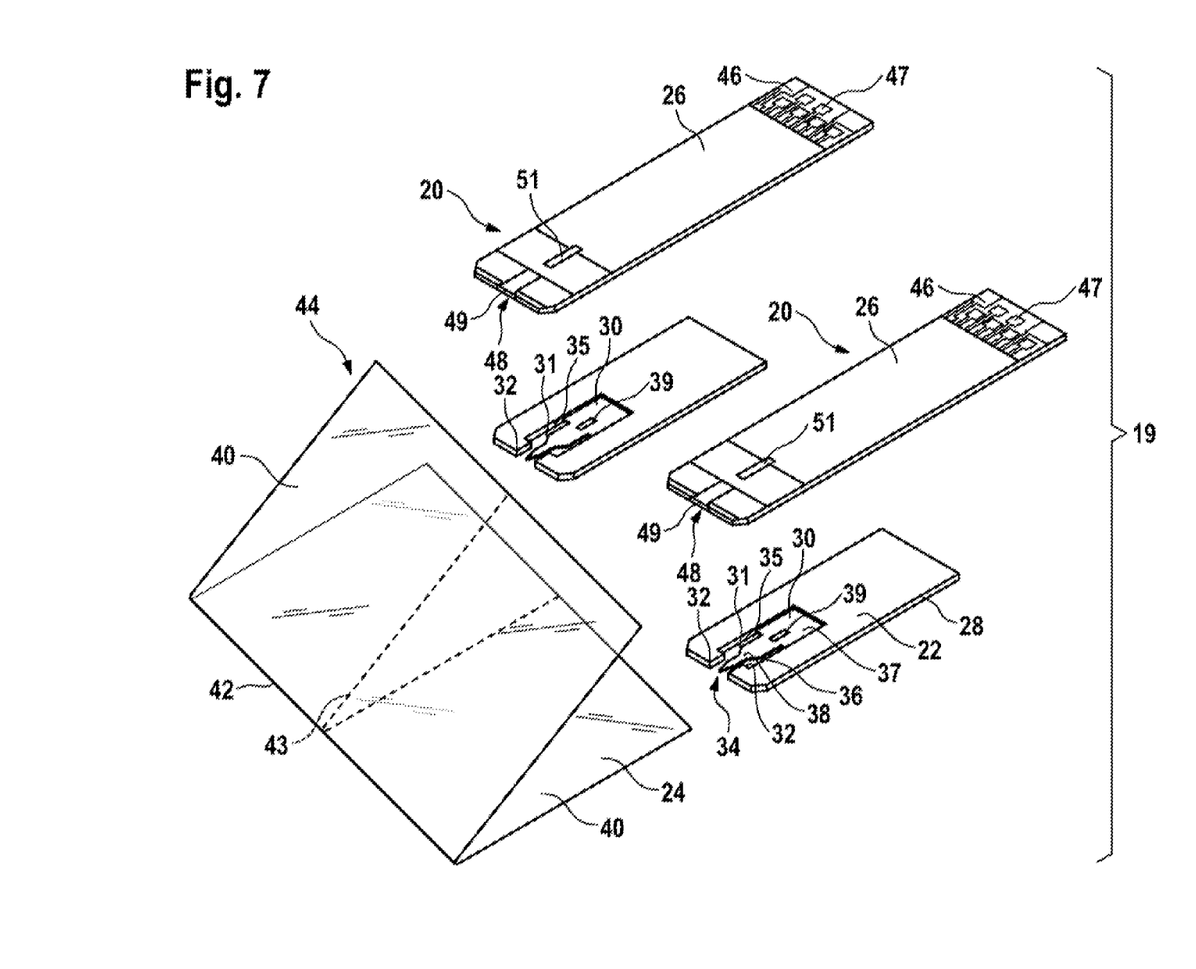
FIG. 7 shows the joining of lancet and test element into a lancet integrated test element (LIT) which are sealed together by laser sealing between at least one foil.

With reference to FIG. 7, after the lancet assembly 22 is formed, the lancet assembly 22 can be then packaged within the foil 24. As will be appreciated from the discussion below, the lancet assembly 22 can be packaged in the foil 24 before, during, or after the lancet assembly 22 is sterilized. In the illustrated embodiment, the foil 24 is a sheet of metallic foil, and in another embodiment, the foil 24 is made of plastic. It should be recognized that the foil 24 can be made of other types of materials. During manufacturing, the foil 24 is folded into two foil portions 40 with a crease or fold 42 in between, as is shown in FIG. 7. After folding, the lancet assemblies 22 are sandwiched between the two folds 40 such that the crease 42 closes the cavity opening 34 of the cavity 31 in the lancet assembly 22. The foil portions 40 are secured to the opposite (flat) sides of the lancet assembly 22 so that the lancet 30 is sealed inside the cavity 31 with the cavity opening 34 closed by the crease 42. In one form, an adhesive is used to secure the foil to the guide member 28. Adhesive is applied on the guide member 28 around the cavity 31, but is not applied to the lancet 30 so that the lancet 30 is able to still slide within the cavity 31. Although an adhesive is used in the illustrated embodiment, it should be understood that the foil 24 can be sealed with the guide member 28 in other manners, such as through heat sealing. In the illustrated embodiment, the edges of the foil portions 40 are not sealed together, but it is envisioned that in other embodiments the edges of the foil 24 can be sealed together so as to form a pocket that encloses the entire lancet assembly 22. In still yet another embodiment, instead of folding the foil 24, two foils 24 are joined together with the lancet assembly 22 sandwiched in between.

As depicted, the integrated lancing test elements 20 in one embodiment are formed in a continuous process. In the continuous process, the foil 24 is a continuous band that is rolled off a reel and folded around a continuous band or belt of lancet assemblies 22 that are likewise rolled from a reel. The lancet assemblies 22 are sealed between the foil portions 40 of the foil 24 and the test elements 26 are attached to the sheet 24 in the manner as described above. The foil 24 joins adjacent Lancet integrated test element (LIT) units 20 together to form the continuous LIT tape 19. Between the individual units 20, the foil 24 has folds or weakened lines 43 that allow the tape 19 to be folded in a fan-fold fashion for storage. The fold lines 43 can also be configured to allow individual units 20 to be detached from one another. The foil 24 can be weakened at the fold lines 43 in any number of manners as would occur to those skilled in the art. For example, the sheet 24 can be scored or thinned at the fold line 43, and it is contemplated that the fold line 43 can be continuous or discontinuous. The fold lines 43 can be formed before the lancet assembly 22 is covered by the foil 24 or afterwards. It is envisioned that the fold line 43 in other embodiments can be optional such that the tape 19 naturally folds in a fan-fold or other fashion. In a preferred embodiment this fold line is cut by a laser, when the LIT units should be singularized.

Once joined together, the lancet assembly 22 and the foil 24 form a lancet package or packet 44. As mentioned before, the lancet assembly 22 can be sterilized before being enclosed in the foil 24 or afterwards. The lancet assembly 22 can be sterilized through any number of sterilization techniques as would occur to those skilled in the art, such as through chemical, heat, and/or radiation sterilization techniques, to name a few. It should be understood that all or part of the lancet assembly 22 can be sterilized. For instance, only the lancet 30 and cavity 31 can be sterilized, if so desired. In another embodiment, the lancet assembly 22 is sterilized after the lancet assembly 22 is packaged inside the lancet package 44. In one form, a radiation sterilization technique is used once the lancet 30 is enclosed by the foil 24. With the lancet package 44, sterilization of the lancet assembly 22 can occur without exposing the test element 26 to the undesirable affects of lancet sterilization. Consequently, the lot specific calibration data can be generated before the lancet package 44 is attached to the test element.

In the illustrated embodiment, the test element 26 is an electro-chemical type test element. In one particular form, the test element 26 includes a modified version of any of the ACCU-CHEK® brand test elements (Roche Diagnostics GmbH), but it is envisioned that other types of test elements can be used. For example, the test element 26 in other embodiments can include an optical type test element or can analyze fluid samples in other manners. At one end, the test element 26 in the illustrated embodiment includes a connection portion 46 with electrical contacts 47 that transmit sample readings to a meter. Opposite the connection portion 46, the test element 26 has a capillary channel 48 with a capillary opening 49 that is configured to draw a body fluid sample from an incision formed by the lancet 30 via capillary action. As should be appreciated, the test element 26 inside the capillary channel 48 includes an analysis region that includes electrodes, such as working, counter and reference electrodes, and reagents for analyzing the fluid sample. In one form, the connection portion 46 is connected to a meter, and the sample readings from the electrodes in the analysis region are transmitted to the meter via the electrical contacts.

As briefly noted before, the sterilized lancet package 44 is attached to the test element 26 to form the integrated lancing test element unit 20. As depicted, the lancet package 44 is attached at the end of the test element 26 proximal to the capillary opening 49 of the capillary channel 48. In particular, the cavity opening 34 of the lancet assembly 22 and the capillary opening 49 of the test element 26 are positioned near one another in a side-by-side relationship so that when the lancet 30 forms the incision, the capillary channel opening 49 is positioned in close proximity to collect the body fluid. The test element 26 is attached to the exterior of the foil 24 enclosing the lancing member 22 to complete the integrated test element 20. The test element 26 in one form is attached to the lancet package 44 through an adhesive, but it should be recognized that the test element 26 and lancet package 44 can be attached in other manners. In one form, the lancet package 44 is attached to the test element 26 such that the end edges of both are aligned with another. However, in other embodiments the edges of the lancet package 44 and the test element 26 can be offset from one another. For example, the edge of the lancet package 44 in the illustrated embodiment, as is demarked by crease, in form of a third portion 42, is recessed slightly from the edge of the test element 26 at the capillary opening 49. By having the lancet package 44 recessed, fluid flow to the capillary channel opening 49 is promoted. In another example, the foil 24 is positioned such that the crease 42 extends past the edge of the test element 26. With this example, all or part of the foil 24 can be hydrophobic and/or hydrophilic so as to direct fluid flow towards the capillary channel 48. In one particular form, the foil 24 extends from the test element 26 such that the foil 24 acts like a flexible wicking flag that draws fluid into the capillary channel 48.

To draw the body fluid towards the capillary channel opening 49 and away from the lancet 30, the test element 26 in the illustrated embodiment has a fluid direction notch facing the lancet package 44. In order to enhance fluid flow towards the capillary channel opening 49, the foil 24 can be treated and/or made to be hydrophobic. With the foil 24 being hydrophobic, the foil can squeegee or wipe body fluid from the lancet 30 as the lancet 30 retracts back inside the cavity 31. It is thought that the wiping action of the foil 24 increases the amount of body fluid available for sampling as well as makes the lancet 30 cleaner for disposal purposes. As noted before, with the lancet 30 sealed in the lancet package 44, the risk of cross-contamination between the lancet 30 and the test element 26 is reduced.

In FIG. 7, the test element 26 further defines a relief slot 51 through which a blade tip of a cam arm extends when engaging the lancet 30 during loading and firing. In addition, the relief slot 51 can be used to vent air from the capillary channel 48 as fluid is collected. The length of the relief slot 51 generally approximates the length of the lancing stroke of the firing mechanism used to actuate the lancet 30. When the lancet package 44 is attached to the test element 26, the engagement notch 39 on the lancet 30 is aligned with the relief slot 51 in the test element 26. As is described in greater detail in U.S. Patent Application No. 2006/0200045, the blade tip of a cam arm for the firing mechanism extends through the engagement notch 39 of the lancet 30 as well as into the relief slot 51. When doing so, the blade tip pierces the foil 24. During lancing, the cam arm via the blade extends and retracts the lancet 30 relative to the test element 26. As the lancet 30 extends, the tip 38 of the lancet 30 pierces the foil 24 at crease 42. In one form, the foil 24 at the crease 42 is weakened so as to aid in puncturing by the lancet 30, but in other forms, the crease 42 is not weakened. Once the lancet 30 is retracted back inside the cavity 31, the two foil portions 40 of the foil 24 can hold the lancet 30 inside through friction. By engaging the lancet 30 in such a manner, the risk of accidental puncturing by the integrated lancing test element 22 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques, which do not require the puncturing of the foil 24. As an example, the lancet 30 in another embodiment is magnetized and fired magnetically through a voice coil driver or other magnetic drivers. With the lancet 30 enclosed in the foil both before and after lancing, the risk of contamination is reduced, and the risk of accidental injury is likewise reduced.

What is claimed:

1. A process for manufacturing packaged lancets, comprising the steps of:
   providing a metal sheet comprising a plurality of lancets which are fixed to the metal sheet via at least one predetermined breaking point whereby the lancets comprise a lancet tip and a lancet body;
   positioning the metal sheet relatively to a tape comprising at least one foil for enveloping at least the lancet tip;
   placing at least one lancet onto the tape and pressing the at least one lancet on the tape so that the at least one breaking point is broken and the lancet is no longer connected with the metal sheet;
and before, simultaneously, or afterwards fixing the lancet on the tape,
   removing the metal sheet and enveloping at least the lancet tip with the foil, whereby the foil builds a first and a second portion that overlap at least partly,
   and sealing the at least one foil preferably with a laser beam at least at the edges of the first and second portion of the overlapping foil.

2. A process for manufacturing packaged lancets, comprising the steps of: providing a tape comprising a plurality of lancets comprising a lancet tip and a lancet body,
   enveloping at least the lancet tip with at least one foil, whereby the at least one foil builds a first and a second portion that overlap at least partly,
   applying a force to the foil in such a way that the foil is pressed onto the lancet by a first component of the force in a first direction and, moreover, by a second component of the force in a second direction perpendicular to the first direction so that the first and second portion of the foil overlaps and at least one portion of the foil is flattened towards the end of the lancet opposite to the lancet tip, and
   sealing the at least one foil preferably with a laser beam at least at the edges of the first and second portion of the overlapping foil.

3. The process according to claim 2, whereby one foil covers a first side of the tape and a second foil covers a second side of the tape.

4. The process according to claim 2, whereby a first portion of the foil covers a first side of the tape and a second portion covers a second side of the tape wherein the first and second portion are connected by a third portion which is located in front of the lancet tip.

5. The process of claim 2, wherein the sealing of the foil is established with a laminar laser sealing process.

6. The process of claim 2, wherein the tape is cut by the laser to separate the lancets.

7. The process of claim 6, wherein the sealing of the foil is established by the laser when the tape is cut with the laser.

8. The process according to claim 7, using different energy rates for the sealing and the cutting of the lancets.

9. The process according to claim 2, wherein the tape is constructed of a polymer, preferentially polyester.

10. The process according to claim 2, with the additional step of sterilizing the lancet.

11. The process according to claim 2, wherein the lancet body is attached to a test element.

12. A process according to claim 2, wherein the force is applied by air brusher.

13. The process according to claim 2, wherein the force is applied in a defined angle relatively to the lancet tape.

14. A process according to claim 13 the angle is adjustable preferably as a function of the air pressure.

15. A process of manufacturing a device for analyzing a component in a body fluid, comprising:
   providing a lancet with a lancet tip and a lancet body and at least one foil, that envelopes at least the tip of the lancet whereby the at least one foil builds a first and a second portion that overlap each other at least partly, wherein the foil is sealed after enveloping at least a part of the lancet by treating at least the edges built by the two partly overlapping portions of the at least one foil preferably with a laser to keep at least the lancet tip in a hermetic surrounding; and
   joining the lancet with a test element comprising a body fluid application field before or after sealing the device.

* * * * *